(12) United States Patent
McNamara et al.

(10) Patent No.: US 6,593,296 B1
(45) Date of Patent: Jul. 15, 2003

(54) STABILIZED GROWTH HORMONE FORMULATION AND METHOD OF PREPARATION THEREOF

(75) Inventors: Michael Kevin McNamara, Victoria (AU); William Neil Charman, Victoria (AU); Susan Ann Charman, Victoria (AU)

(73) Assignees: CSL Limited, Victoria (AU); Monash University, Victoria (AU)

( * ) Notice: Subject to any disclaimer, the term of this patent is extended or adjusted under 35 U.S.C. 154(b) by 0 days.

(21) Appl. No.: 09/125,267

(22) PCT Filed: Feb. 12, 1997

(86) PCT No.: PCT/AU97/00075
§ 371 (c)(1),
(2), (4) Date: Mar. 25, 1999

(87) PCT Pub. No.: WO97/29767
PCT Pub. Date: Aug. 21, 1997

(30) Foreign Application Priority Data

Feb. 12, 1996 (AU) .............................................. PN8012

(51) Int. Cl.⁷ ...................... A61K 38/00; A61K 38/24; C07K 14/00
(52) U.S. Cl. .......................... 514/12; 514/2; 514/970; 530/324; 530/350; 530/399
(58) Field of Search .............................. 514/12, 2, 970; 530/324, 350, 399

(56) References Cited

U.S. PATENT DOCUMENTS

| | | | |
|---|---|---|---|
| 5,096,885 A | 3/1992 | Pearlman et al. | 514/12 |
| 5,283,236 A | 2/1994 | Chiou | 514/2 |

FOREIGN PATENT DOCUMENTS

| | | |
|---|---|---|
| AU | 60733/86 | 2/1987 |
| AU | 20051/88 | 2/1989 |
| AU | 42432/89 | 4/1990 |
| EP | 0 211 601 | 2/1987 |
| EP | 0 303 746 | 2/1989 |
| GB | 0 131 864 | 9/1990 |
| WO | 93/19776 | 10/1993 |
| WO | 94/03198 | 2/1994 |
| WO | WO95//14037 | * 5/1995 |

OTHER PUBLICATIONS

Patent Abstract of Japan, C–846, pp. 85, Saeki, "new Pharmaceutical of Peptide or Protein For Oral Medicine", JP No. 3–86834, (Apr. 11, 1991) Abstract only.

Katakam et al., "Effect of Surfactants on The Physical Stability Of Recombinant Human Growth Hormone", *Journal of Pharmaceutical Sciences*, vol. 84(6):713–716, (1995).

* cited by examiner

*Primary Examiner*—Christopher S. F. Low
*Assistant Examiner*—Abdel A. Mohamed
(74) *Attorney, Agent, or Firm*—Foley & Lardner

(57) ABSTRACT

A method for the preparation of a stable, liquid formulation of growth hormone, comprising growth hormone, a buffer and a stabilizing effective amount of at least one stabilizing agent selected from the group consisting of: (i) polyethylene-polypropylene glycol non-ionic surfactants, (ii) taurocholic acid or salts or derivatives thereof, and (iii) methyl cellulose derivatives, wherein the method comprises admixing the growth hormone with the buffer and the stabilizing agent(s) under conditions such that the growth hormone is not exposed to concentrations of the buffer or stabilizing agent(s) which are greater than 2× the final concentrations of the buffer or stabilizing agent(s) in the formulation.

18 Claims, 4 Drawing Sheets

STABILIZED GROWTH HORMONE FORMULATION AND METHOD OF PREPARATION THEREOF

CROSS REFERENCE TO RELATED APPLICATIONS

This application is a national phase application of PCT International Application No. PCT/AU97/00075, filed Feb. 12, 1997, which is entitled to priority to Australian patent application PN 8012, filed Feb. 12, 1996.

FIELD OF THE INVENTION

This invention relates to stabilised growth hormone (GH) formulations and in particular to liquid formulations of human growth hormone (hGH) which are stabilized by the incorporation of stabilizing excipients. These liquid formulations of hGH have improved chemical and physical stability. The present invention relates particularly to a method for the preparation of these stabilized GH formulations.

BACKGROUND OF THE INVENTION

The growth hormones of humans and animals are proteins containing approximately 191 amino acids which are found in the anterior pituitary. A major biological action of GH is to promote somatogenesis in young humans and animals and to maintain tissues in older creatures. Organs affected by GH include the skeleton, muscles, connective tissue and the viscera. Growth hormone acts by interacting with specific receptors on the target cell membranes.

Human growth hormone (hGH) is a key hormone involved in the regulation of normal human somatic growth and also affects a variety of physiological and metabolic functions, including linear bone growth, lactation and cellular energy use, among others. Deficiency of hGH in young children leads to short stature, and this condition has been treated by exogenous administration of hGH.

In the past, attention has been focused on determining the molecular functions of the growth hormones of various species. Commercial interest has been strong from both medical and veterinary circles, and the hGH gene has been cloned. Both hGH and a derivative thereof, methionyl-hGH (met-hGH), are now being biosynthetically produced in mammalian and bacterial cell culture systems.

In order for hGH to be available commercially as a therapeutic pharmaceutical preparation, stable formulations must be prepared. Such formulations must be capable of maintaining activity for appropriate storage times, they must be readily formulated and be acceptable for administration by patients.

Human GH has been formulated in a variety of ways. By way of example, U.S. Pat. No. 5,096,885 discloses a stable pharmaceutically acceptable formulation of hGH comprising, in addition to the hGH, glycine, mannitol, a buffer and optionally a non-ionic surfactant, the molar ratio of hGH:glycine being 1:50–200. International Patent Publication No. WO 93/19776 discloses injectable formulations of GH comprising citrate as buffer substance and optionally growth factors such as insulin-like growth factors or epidermal growth factor, amino acids such as glycine or alanine, mannitol or other sugar alcohols, glycerol and/or a preservative such as benzyl alcohol. International Patent Publication No. WO 94101398 discloses a GH formulation containing hGH, a buffer, a non-ionic surfactant and, optionally, mannitol, a neutral salt and/or a preservative.

In European Patent Publication No. 0131864 (and corresponding Australian Patent No. 579016) there is disclosed an aqueous solution of proteins with molecular weight above 8500 daltons, which have been protected from adsorption at interfaces, against denaturing and against precipitation of the protein by addition of a linear polyoxyalkylene chain-containing surface-active substance as a stabilizing agent.

European Patent Publication No. 0211601 discloses a growth promoting formulation comprising an aqueous mixture of growth promoting hormone and a block copolymer containing polyoxyethylene-polyoxypropylene units and having an average molecular weight of about 1,100 to about 40,000 which maintains the fluidity of the growth promoting hormone and its biological activity upon administration. Subsequent European Patent Publication No. 0303746 discloses various other stabilizers for growth promoting hormone in aqueous environments including certain polyols, amino acids, polymers of amino acids having a charged side group at physiological pH and choline salts.

Pharmaceutical preparations of hGH tend to be unstable, particularly in solution. Chemically degraded species such as deamidated or sulfoxylated forms of hGH occur, and dimeric or higher molecular weight aggregated species may result from physical instability (Becker et al (1988) Biotechnol Applied Biochem 10, 326; Pearlman and Nguyen (1989), In D. Marshak and D. Liu (eds), *Therapeutic Peptides and Proteins, Formulations, Delivery and Targeting, Current Communications in Molecular Biology*, Cold-Spring Harbour Laboratory, Cold Spring Harbour, N.Y., pp 23–30; Becker et al (1987) *Biotechnol Applied Biochem* 9, 478).

As a consequence of the instability of hGH in solution, pharmaceutical formulations of hGH tend to be presented in lyophilised form, which must then be reconstituted prior to use. Lyophilisation is often used to maintain bioactivity and biochemical integrity of polypeptides under a range of storage conditions where stability in solution is not adequate, however it would be advantageous to avoid lyophilisation as this is a costly and time-consuming production step. Lyophilised formulations of hGH are reconstituted before use, usually by the addition of a pharmaceutically acceptable diluent such as sterile water for injection, sterile physiological saline or an appropriate sterile physiologically acceptable diluent. Reconstituted solutions of hGH are preferably stored at 4° C. to minimize chemical and physical degradation reactions, however some degradation will occur during such storage which can be for a period of up to 14 days.

A pharmaceutical formulation of hGH provided in a liquid form, particularly one that maintained stability of hGH over a prolonged period of time, would be particularly advantageous. As described above, current liquid formulations are limited in storage time by the products of chemical and physical degradation reactions that occur during processing and storage. The problems associated with dimer formation have been reported in Becker, et al. (1987), supra., and previous attempts to avoid hGH dimer formation have not succeeded.

It is an object of the present invention to provide stable liquid formulations of hGH that do not result in the formation of undesirable aggregated species or cause chemical changes that reduce biological activity or alter receptor recognition. Another object is to provide a formulation that may be delivered via the needleless injector for subcutaneous injection, or aerosolised for pulmonary use.

SUMMARY OF THE INVENTION

According to the present invention, there is provided a method for the preparation of a stable, liquid formulation of growth hormone comprising growth hormone, a buffer and a stabilizing effective amount of at least one stabilizing agent selected from the group consisting of:

(i) polyoxyethylene-polyoxypropylene block copolymer non-ionic surfactants,
(ii) taurocholic acid or salts or derivatives thereof, and
(iii) methylcellulose derivatives, wherein the method comprises admixing the growth hormone with the buffer and the stabilizing agent(s) under conditions such that the growth hormone is not exposed to concentrations of the buffer or stabilizing agent(s) which are greater than 2× the final concentrations of the buffer or stabilizing agent(s) in the formulation.

The present invention also extends to a stable, liquid formulation of growth hormone, prepared by the method as broadly described above.

In yet another aspect, the invention also extends to a stable, liquid formulation of growth hormone, comprising growth hormone, a buffer and a stabilizing effective amount of at least one stabilizing agent selected from taurocholic acid or salts or derivatives thereof, and methyl cellulose derivatives.

Throughout this specification, unless the context requires otherwise, the word "comprise", or variations such as "comprises" or "comprising", will be understood to imply the inclusion of a stated integer or group of integers but not the exclusion of any other integer or group of integers.

In a particularly preferred embodiment, this invention provides a method for the preparation of a stabilized, pharmaceutically acceptable liquid formulation of human growth hormone comprising:

(a) a pharmaceutically effective amount of hGH,
(b) 0.01–5.0% w/v of at least one stabilizing agent selected from the group broadly defined above, and
(c) a pharmacologically acceptable buffer.

Preferably, this formulation comprises 0.05–2.0% w/v, more preferably 0.08–1.0% w/v, of the stabilizing agent(s).

Particularly preferred stabilizing agents are Pluronic polyols, taurocholic acid and its salts, and hydroxypropylmethyl cellulose.

The stabilized, liquid formulation of growth hormone preferably also contains a pharmacologically acceptable buffer such as a phosphate or citrate buffer, at a concentration of 2.5–50 mM, most preferably 10–20 mM.

The pH of the formulation is preferably from 5.0 to 7.5, more preferably from 5.0 to 6.8, even more preferably from 5.2 to 6.5, and most preferably from 5.4 to 5.8.

In the preparation of the stabilized, liquid formulation of growth hormone, the growth hormone is admixed with the buffer under conditions such that the growth hormone is not exposed to buffer concentrations greater than 2× the final concentration of buffer in the formulation, and subsequently the stabilizing agent(s) is added to the admixture under corresponding conditions.

In a particularly preferred method of preparation of the stabilized, liquid formulation of growth hormone, exposure of growth hormone is restricted to concentrations of phosphate or citrate buffer and Pluronic polyols not greater than 2× the final concentration of each component.

The present invention also extends to a method for treatment of a human or animal patient in need of growth hormone, which comprises administration to said patient of a pharmaceutically effective amount of a stable, liquid formulation of growth hormone as broadly described above.

The GH liquid formulation may be administered by bolus injection, with an aerosol device or needleless injector gun or by continuous IV infusion.

In the present context, references to "growth hormone" are intended to include all species of GH including human, bovine, porcine, ovine and salmon, among others, particularly hGH, as well as biologically active derivatives of GH. Derivatives of GH are intended to include GH of human or animal species with variations in amino acid sequence, such as small deletions of amino acids or replacement of amino acids by other amino acid residues. Also included are truncated forms of GH and derivatives thereof, as well as GH with amino acid additions to the amino- or carboxyl-terminal end of the protein, such as methionyl-hGH. Another type of hGH modification is that formed through the covalent addition of polyethylene glycol to reactive hGH amino acids (Davis et al., U.S. Pat. No. 4,179.,337).

DETAILED DESCRIPTION OF THE INVENTION

The method of preparation of liquid formulations of GH and stabilizing agents provided by the present invention results in a stable liquid GH formulation suitable for prolonged storage at temperatures below freezing and above freezing, and for, therapeutic administration. Therapeutic formulations containing these stabilizing agents are stable, while still allowing therapeutic administration of the formulation.

According to a preferred embodiment of the present invention the GH is hGH.

(1) Human Growth Hormone Compositions

The terms "human growth hormone" or "hGH" denote human growth hormone produced, for example, by extraction and purification of hGH from natural sources, or by recombinant cell culture systems. The sequence of hGH and its characteristics are described, for example, in Hormone Drugs, Gueriguigan et al, USP Convention, Rockville, Md. (1982). As described above, the terms also cover biologically active human growth hormone equivalents that differ in one or more amino acids in the overall sequence of hGH, including in particular met-hGH. The terms are also intended to cover substitution, deletion and insertion amino acid variants of hGH or post translational modifications. The hGH used in the formulations of the present invention is generally produced by recombinant means as previously discussed.

A "pharmaceutically effective amount" of GH, particularly hGH, refers to that amount which provides therapeutic effect in various administration regimens. The compositions of the present invention may be prepared containing amounts of GH at least about 0.1 mg/ml up to about 20 mg/ml or more, preferably from about 1 mg/ml to about 10 mg/ml, more particularly from about 1 mg/ml to about 5 mg/ml.

(2) Buffer and pH

The buffer may be any pharmaceutically acceptable buffering agent such as phosphate, tris-HCl, citrate and the like. The preferred buffer is a phosphate or citrate buffer. A buffer concentration greater than or equal to 2 mM and less than 50 mM is preferred, most advantageously 10–20 mM. Suitable pH ranges, adjusted with buffer, for the preparation of the formulations hereof are from about 5 to about 7.5, most advantageously about 5.6. The formulation pH should be less than 7.5 to reduce deamidation of GH.

(3) Stabilizing Agents

In accordance with the present invention, the formulation contains one or more stabilizing agents for enhanced GH stability. The stabilizing agent may be a polyoxyethylene-polyoxypropylene block copolymer non-ionic surfactant such as a Pluronic polyol, for example, Pluronics F127, F68, L64, PE6800 and PE6400, a bile salt such as a taurocholic acid salt or derivative thereof, or a methylcellulose derivative such as hydroxypropylmethylcellulose (HPMC). The formulation may contain a single stabilizing agent or a combination of two or more thereof.

The concentration of stabilizing agent(s) added will be determined by the selection of buffer and pH, but advantageously would be in the range of 0.01% to 5.0%, more preferably 0.05 to 2.0% and even more preferably 0.08 to 1.0%, on a weight to volume basis. The use of stabilizing agents improves formulation stability when subjected to prolonged storage over a range of temperatures, including below freezing and above freezing, or when the formulation is subjected to interfacial stress.

The stabilizing agent(s) improve formulation stability to interfacial stress with increasing concentration. However, increased stabilizing agent(s) concentration reduces chemical stability. In accordance with the present invention, the concentration of stabilizing agent(s) is optimised to achieve high stability to interfacial stress with minimum additional chemical instability.

(4) Preferred Formulation of Stabilizing Agents and hGH

In the preparation of a formulation in accordance with the present invention, one or more stabilizing agents are added to a hGH liquid formulation. As described above, during formulation, the growth hormone is exposed to buffer concentrations no greater than 2× the final concentration of buffer, and preferably the stabilizing agent(s) are added to the formulation immediately prior to final volume adjustment. The resulting formulations have enhanced stability to denaturation and are not susceptible to undesirable reactions that may be met during processing and storage. As used herein, the term processing includes filtration, filling of hGH solutions into vials and other manipulations involved in production of the formulations.

Liquid formulations of hGH for therapeutic administration may be prepared by combining hGH and stabilizing agents having the desired degree of purity with physiologically acceptable excipients, buffers or preservatives (*Remington's Pharmaceutical Sciences*, 16th Edition, Osol, A. Ed (1980). Acceptable excipients are those which are nontoxic to the patient at the concentrations and dosages employed, and include buffers, preservatives, antioxidants, pH and tonicity modifiers.

The liquid formulation of growth hormone may also include one or more other stabilizing excipients if desired. Additional stabilizing excipients may include, for example, amino acids such as glycine or alanine, mannitol or other sugar alcohols, or glycerol. In addition, the liquid formulation may include other growth factors such as insulin-like growth factors or epidermal growth factor.

The preferred embodiment of the invention provides a means for effectively stabilizing hGH. The preferred formulation contains one or more stabilizing agents selected from Pluronic polyols, taurocholic acid or salts or derivatives thereof, and methylcellulose derivatives. The formulation preferably contains substantially pure hGH free of contaminating peptides or proteins or infectious agents found in humans. Formulations of this preferred embodiment may additionally contain pharmaceutically acceptable additives. These include, for example, buffers, isotonicity and pH modifiers, chelating agents, preservatives, antioxidants, cosolvents and the like, specific examples of these could include citrate salts, phosphate salts and the like. A preservative may be added where the anticipated use of the formulation may compromise sterility, and in such a case a pharmaceutically acceptable preservative such as benzyl alcohol or phenol may be used.

The increased stability of hGH provided by the formulation prepared in accordance with the present invention permits a wider use of hGH formulations that may be more concentrated than those commonly in use in the absence of stabilizing agents. For example, stabilized hGH liquid formulations also reduce the incidence of surface induced denaturation of hGH that occurs during aerosolisation or needleless injection of an hGH formulation. Further optimal dispensing of the hGH formulations may be made wherein the hGH formulations of the present invention are dispensed into vials at 1–50 mg/vial, preferably 2–25 mg/vial, and more preferably 3–10 mg/vial. The increased stability of hGH formulations permits long term storage at an appropriate temperature, such as below freezing (most preferably at −20° C.), or above freezing, preferably at 2–8° C., most preferably at 4° C.

Formulations of hGH to be used for in vivo administration must be sterile. This is readily accomplished by filtration through sterile filtration membranes.

Therapeutic hGH liquid formulations generally are placed into a container having a sterile access port, for example, an intravenous solution bag or vial having a stopper which can be pierced by a hypodermic injection needle.

The route of administration of the hGH liquid formulations in accordance with the present invention is in accord with known practice, e.g. injection or infusion by intravenous, intraperitoneal, intracerebral, intramuscular, intraocular, intraarterial, or intralesional routes, or by continuous IV infusion.

Further features of the present invention will be apparent from the following Examples, and the accompanying drawings.

EXAMPLES

Example 1

Methods for Screening Stabilizing Agents

Figures 1A, 1B, 1C:
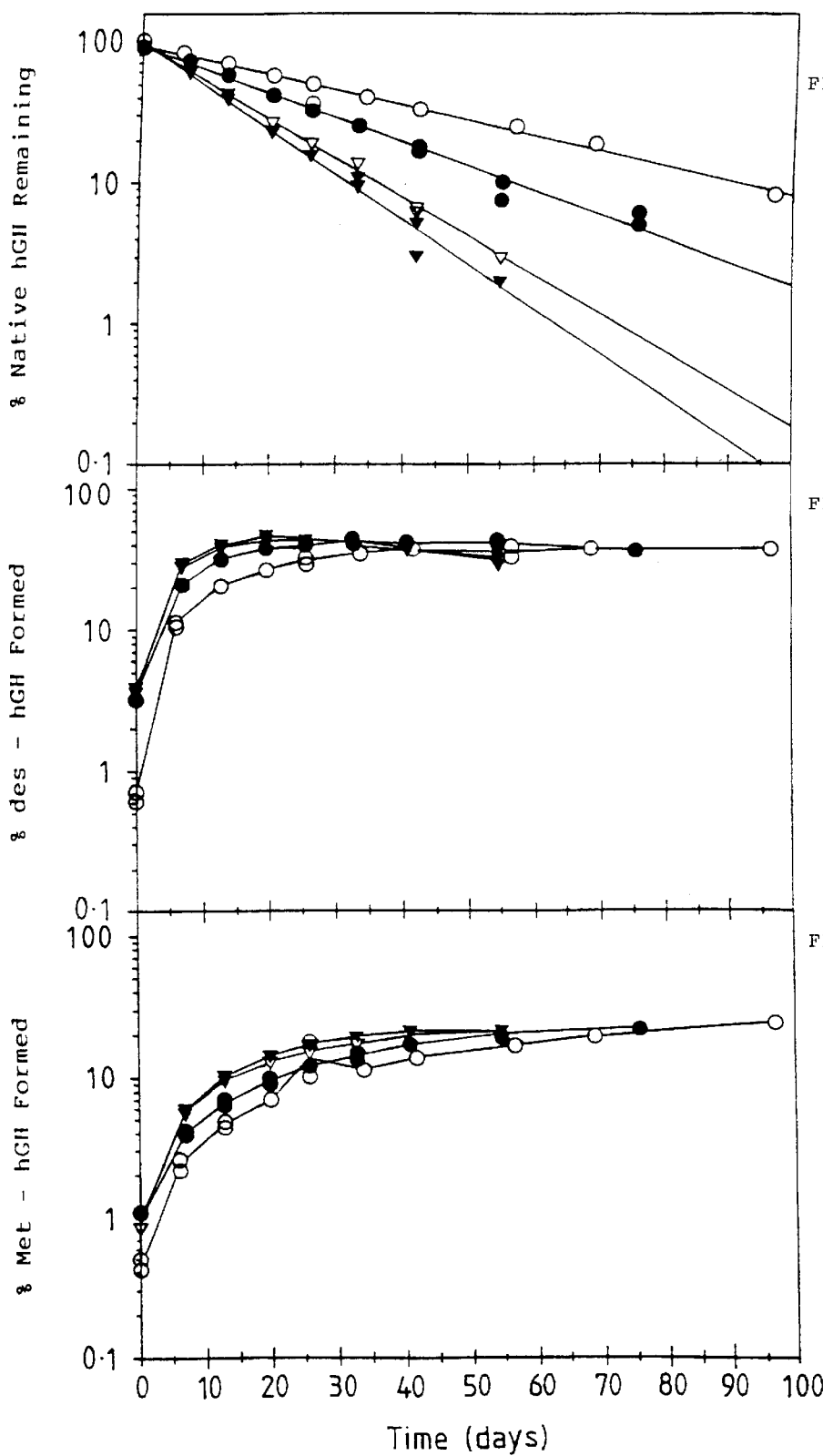
FIG. 1 shows the chemical stability of hGH (1.5 mg/ml) in 5 mM phosphate buffer, pH 6.0–7.5.

The ability of stabilizing agents to reduce or prevent GH and in particular hGH aggregation in response to interfacial stress has been evaluated using a rapid aggregation method and analyzed by size exclusion chromatography (SEC). Chromatography of hGH was conducted using two TSK G3000SW columns (7.8 mm i.d.×300 mm, Toyo Sodo, Japan) in series. The mobile phase consisted of 0.1 M phosphate, pH 7.0 buffer and was pumped at a flow rate of 0.9 ml/min. Elution of hGH was detected by UV absorbance at 214 nm using a sample volume of 20 μl.

The rapid aggregation method involved the introduction of a high air/water interface by vortex agitation of hGH solutions at constant speed for 15–60s in capped polypropylene tubes (11 mm i.d.×74 mm). Samples were equilibrated for 30 min at room temperature to allow precipitation to proceed, then were filtered through 0.2 μm cellulose acetate microcentrifuge filters and the filtrate was analyzed by SEC. Control solutions of each sample that did not receive treatment were included in SEC analysis.

The amount of total soluble hGH remaining (peak area of monomeric and higher molecular weight species) was expressed as a percentage of the total peak area (due to hGH) of the appropriate untreated control solution.

Table 1 shows the effect of various stabilizing agents on the extent of aggregation of hGH induced by interfacial stress at pH 7.0.

Table 2 shows the effect of various stabilizing agents on the extent of aggregation of hGH induced by interfacial stress at pH 6.0.

Table 3 shows the effect of various stabilizing agents on the extent of aggregation of hGH induced by interfacial stress at pH 5.6.

Table 4 shows the effect of isotonicity adjustment on the extent of aggregation of hGH (1.5 mg/ml) in various buffers at pH 5.6.

Table 5 shows the effect of various stabilizing agents on the extent of aggregation of hGH induced by freeze-thawing at pH 5.6.

As shown in the accompanying tables, a number of excipients were very effective at reducing or preventing aggregation of hGH induced by interfacial stress. Pluronic polyols provided near quantitative protection at concentrations above 0.05% w/v with monomeric hGH only remaining. Taurocholate, provided near quantitative protection at concentrations above 0.02% w/v with monomeric hGH only remaining. Taurodeoxycholate was not suitable as a stabilizer at a pH of 5.6 as it caused dimerisation of hGH in the absence of interfacial stress.

TABLE 1

Aggregation of hGH (1.5 mg/ml) in the presence of excipients at pH 7.0 induced by interfacial stress.

| Excipient | Concentration (mM) | (% w/v) | % Total Soluble hGH Remaining (n = 2, SEC analysis) | Species of hGH Remaining |
|---|---|---|---|---|
| buffer | control | | 7.0 ± 1.15 | (mean ± sd, n = 5) |
| Pluronic Polyols: | | | | |
| Pluronic F-127 | 1.4 | 1.75 | 100, 99.8 | monomer only in |
|  | 3.2 | 4.0 | 100, 100 | all samples |
| Taurocholic Acid Derivatives: | | | | |
| Taurocholate | 1.3 | 0.07 | 75.3, 68.5 | monomer only in |
|  | 5 | 0.27 | 100, 100 | all samples |
|  | 75 | 4.0 | 100, 100 | |
| Taurodeoxycholate | 0.4 | 0.02 | 13.7, 15.0 | monomer only in |
|  | 2 | 0.11 | 100, 100 | all samples |
|  | 30 | 1.6 | 100, 100 | |
| Methyl cellulose derivatives: | | | | |
| Hydroxypropylmethyl-cellulose (HPMC) | 0.01 | 0.1 | 44.1, 47.1 | monomer only in |
|  | 0.05 | 0.5 | 98.9, 99.4 | all samples |

TABLE 2

Aggregation of hGH (1.5 mg/ml) in the presence of excipients at pH 6.0 induced by interfacial stress.

| Excipient | Concentration (mM) | (% w/v) | % Total Soluble hGH Remaining (n = 2, SEC analysis) | Species of hGH Remaining |
|---|---|---|---|---|
| buffer | control | | 2.4 ± 2.05 | (mean ± sd, n = 6) |
| Pluronic Polyols: | | | | |
| Pluronic F-127 | 0.01 | 0.01 | 3.34, 1.12 | monomer only in all samples |
|  | 0.04 | 0.05 | 93.7, 91.9 | |
|  | 0.08 | 0.1 | 100, 100 | |
|  | 0.4 | 0.5 | 100, 99.6 | |

TABLE 2-continued

Aggregation of hGH (1.5 mg/ml) in the presence of excipients at pH 6.0 induced by interfacial stress.

| Excipient | Concentration (mM) | (% w/v) | % Total Soluble hGH Remaining (n = 2, SEC analysis) | Species of hGH Remaining |
|---|---|---|---|---|
| Pluronic F-68 | 1.6 | 2.0 | 98.5, 97.7 | monomer only in all samples |
|  | 0.01 | 0.01 | 1.2, 2.1 |  |
|  | 0.06 | 0.05 | 86.4, 97.5 |  |
|  | 0.12 | 0.1 | 98.6, 100 |  |
|  | 0.6 | 0.5 | 100, 99.7 |  |
| Pluronic L-64 | 0.03 | 0.01 | 1.1, 1.4 | monomer only in all samples |
|  | 0.17 | 0.05 | 93.7, 79.4 |  |
|  | 0.35 | 0.1 | 100, 100 |  |
|  | 1.7 | 0.5 | 100, 98.4 |  |
| Pluronic PE-6800 | 0.12 | 0.1 | 98.7, 99.2 | monomer only in all samples |
|  | 0.6 | 0.5 | 99.6, 99.6 |  |
|  | 2.4 | 2.0 | 100, 99.0 |  |
| Pluronic PE-6400 | 0.35 | 0.1 | 100, 100 | monomer only in all samples |
|  | 1.7 | 0.5 | 100, 100 |  |
| Taurocholic Acid Derivatives: |  |  |  |  |
| Taurocholate | 1.3 | 0.07 | 16.8, 11.9 | monomer only in all samples |
|  | 6 | 0.34 | 98.5, 100 |  |
|  | 15 | 0.84 | 97.8, 99.3 |  |
|  | 25 | 1.4 | 98.7, 99.1 |  |
| Taurodeoxycholate | 0.4 | 0.02 | 9.2, 4.9 |  |
|  | 2 | 0.10 | 22.6, 22.0 | approximately 0.5% dimer |
|  | 6 | 0.31 | 87.2, 88.3 |  |
|  | 12 | 0.63 | 99.5, 100 | approximately 4% dimer |
| Methyl Cellulose Derivatives: |  |  |  |  |
| HPMC | 0.01 | 0.1 | 28.6, 24.0 | monomer only in all samples |
|  | 0.03 | 0.25 | 58.6, 63.4 |  |
|  | 0.04 | 0.4 | 91.9, 93.6 |  |

TABLE 3

Aggregation of hGH (1.5 mg/ml) in the presence of excipients at pH 5.6 induced by interfacial stress.

| Excipient | Concentration (mM) | (% w/v) | % Total Soluble hGH Remaining (n = 2, SEC analysis) | Species of hGH Remaining |
|---|---|---|---|---|
| buffer | control |  | 0.79, 1.16 | (mean ± sd, n = 2) |
| Pluronic Polyols: | 0.04 | 0.05 | 69.6, 53.8 | 2% dimer present |
|  | 0.08 | 0.1 | 99.5, 99.7 | 0.7% dimer |
| Pluronic F-127 | 0.4 | 0.5 | 99.5, 98.8 | present monomer only |
| Pluronic F-68 | 0.06 | 0.05 | 69.9, 66.8 | monomer only in all samples |
|  | 0.12 | 0.01 | 99.3, 98.1 |  |
|  | 0.6 | 0.5 | 99.8, 100 |  |
| Taurocholic Acid Derivatives: |  |  |  |  |
| Taurocholate | 5 | 0.27 | 99.7, 99.2 | monomer only in all samples |
|  | 10 | 0.54 | 100, 100 |  |
|  | 25 | 1.4 | 99.4, 100 |  |
| Taurodeoxycholate | 2 | 0.10 | 95.7, 91.8* |  |
|  | 6 | 0.32 | 92.1, 87.8* | 7% dimer present |
|  | 12 | 0.63 | 91.6, 84.4* | 27% dimer present 34% dimer present |
| Methyl Cellulose Derivatives: |  |  |  |  |

TABLE 3-continued

Aggregation of hGH (1.5 mg/ml) in the presence of excipients at pH 5.6 induced by interfacial stress.

| Excipient | Concentration (mM) | (% w/v) | % Total Soluble hGH Remaining (n = 2, SEC analysis) | Species of hGH Remaining |
|---|---|---|---|---|
| HPMC | 0.01 | 0.1 | 5.8, 2.1 | monomer only in all samples |
|  | 0.03 | 0.25 | 34.8, 36.7 |  |
|  | 0.04 | 0.4 | 88.8, 88.4 |  |

*in the presence of taurodeoxycholate, dimerisation occurred in the absence of interfacial stress Aggregation characteristics of hGH (1.5 mg/ml, pH 5.6) in citrate or phosphate (5 or 20 mM) buffers with or without added sodium chloride (to isotonicity) were investigated as aggregation has been reported to be dependent on phosphate concentration (Pearlman and Nguyen, 1992, *J. Pharm. Pharmacol.* 44: 178–185).

The experimental method as described previously was followed with modification of treatment time (15 sec).

Aggregation of hGH (1.5 mg/ml in 20 mM isotonic citrate buffer, pH 5.6) in the presence of excipients induced by freeze-thawing was investigated. Samples of hGH (100 µl) in the presence of various excipients were frozen at −20° C. for 24 hr then thawed at room temperature and equilibrated for 30 min to allow precipitation to proceed. Analysis of filtered samples was conducted by SEC as described previously.

TABLE 5

Aggregation of hGH (1.5 mg/ml) in the presence of excipients at pH 5.6 induced by freeze-thawing.

| Excipient | Concentration (mM) | (% w/v) | % Total Soluble hGH Remaining (n = 2, SEC analysis) | Species of hGH Remaining |
|---|---|---|---|---|
| buffer | control |  | 98.8, 95.5 | monomer only |
| Pluronic Polyols: |  |  |  |  |
| Pluronic F-127 | 0.08 | 0.1 | 95.9, 97.5 | monomer only |
| Pluronic F-68 | 0.12 | 0.1 | 100, 100 | monomer only |
| Taurocholic Acid Derivatives: |  |  |  |  |
| Taurocholate | 5 | 0.27 | 97.9, 100 | monomer only |
| Taurodeoxycholate | 2 | 0.1 | 95.7, 91.8 | contains 24% dimer |
| MethylCellulose Derivatives: |  |  |  |  |
| HPMC | 0.03 | 0.25 | 97.2, 97.3 | monomer only |

TABLE 4

Aggregation of hGH (1–5 mg/ml) in various buffer systems at pH 5.6.

|  | % Total Soluble hGH Remaining[a] | | Species of |
|---|---|---|---|
| Buffer system | no added NaCl | added NaCl | hGH present |
| 5 mM phosphate | —[b] | 44.5, 30.3 | monomer only |
| 5 mM citrate | 18.9, 21.2 | 44.3, 46.4 | monomer only |
| 20 mM phosphate | 28.5, 33.1 | 43.1, 38.7 | monomer only |
| 20 mM citrate | 24.6, 33.2 | 55.5, 50.0 | monomer only |

[a]monomer plus higher molecular weight species
[b]insufficient hGH solubility.

Aggregation of hGH was not found to be dependent on the nature of the buffer or buffer concentration. Aggregation of hGH was inversely related to ionic strength (when adjusted with NaCl).

Aggregation of hGH after freeze-thawing was not extensive but was not increased by the addition of excipients.

Example 2

FIG. 1 is a representative profile of the chemical stability of hGH (1.5 mg/ml) in 5 mM phosphate buffer, pH 6.0–7.5 (stored at 40° C.). Degraded samples were analyzed by reversed-phase high performance liquid chromatography (RP-HPLC) according to the method described in the United States Pharmacopoeia (USP 1990) using a Vydac C4 column. Degradation products were identified according to the method described in U.S. Pharmacopeial Previews, November-December, 1990, as desamido-hGH or oxidised hGH. The amount of native hGH (Panel A), desamido-hGH (Panel B) and oxidised-hGH (Panel C) present in a degraded sample was expressed as a percentage of peak area (for native hGH or degraded species) relative to the total peak area (due to hGH) for pH 6.0 (○), pH 6.5 (●), pH 7.0 (▽) and pH 7.5 (▼).

Loss of native hGH was found to follow first order kinetics in the pH range 6.0–7.5 and Arrhenius behaviour in the temperature range of 8–40° C. The first order rate constants at 40° C. were found to range from $2.4 \times 10^{-2}$ day$^{-1}$ at pH 6.0 to $7.4 \times 10^{-2}$ day$^{-1}$ at pH 7.5 Deamidation and oxidation were the major routes of degradation of hGH consistent with published reports (Pearlman and Nguyen, 1989, supra). Desamido-hGH formed at a faster rate than oxidised hGH. Chemical stability was enhanced at a pH value of 6.0 or below.

Figure 2A:
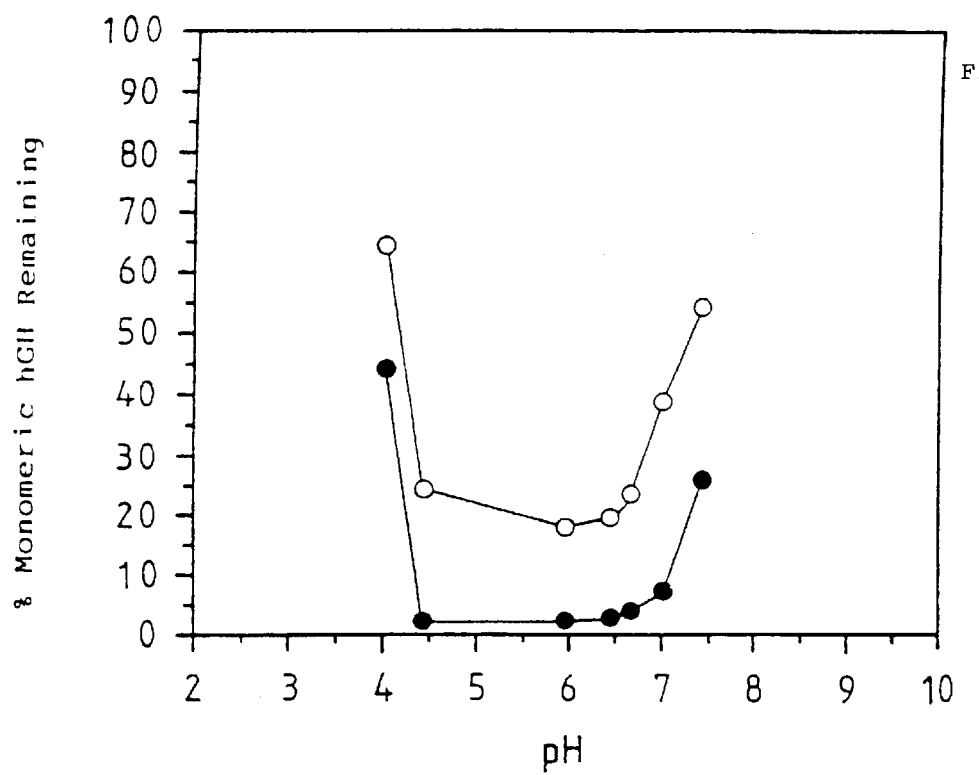
FIG. 2 shows the dependence of aggregation of hGH (2 mg/ml in 10 mM acetate buffer, pH 4.1–4.5 or 5 mM phosphate buffer, pH 6.0–7.5) induced through interfacial stress (vortex agitation) on solution pH.
Figure 2B:
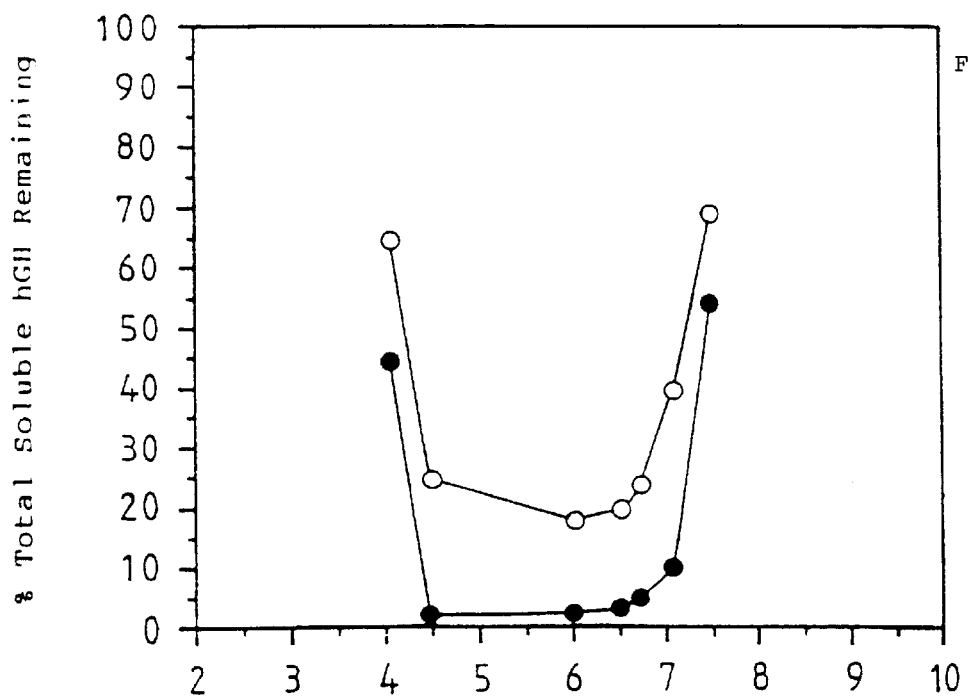

FIG. 2 shows aggregation and precipitation of hGH (2 mg/ml) in 10 mM acetate buffer (pH 4.14.5) or 5 mM phosphate buffer (pH 6.6–7.5) induced through interfacial stress using methods as described in Example 1. The amount of monomeric hGH (peak area due to monomer) or total soluble hGH (peak area due to monomer plus higher order aggregated species) remaining was expressed as a percentage relative to the peak area of the appropriate untreated control solution. The data represent the amount of soluble monomeric hGH (Panel A) or total soluble hGH (Panel B) remaining after vortexing for 30 s (○) or 60 s (●).

Aggregation and subsequent precipitation of hGH was maximal in the region of pH 5 to 6. Only monomeric hGH remained in solution after interfacial stress in the pH range of 4.16.0. Soluble aggregated species (dimer and higher order aggregates) were present mainly in the pH range of 7.0–7.5.

Figure 3:
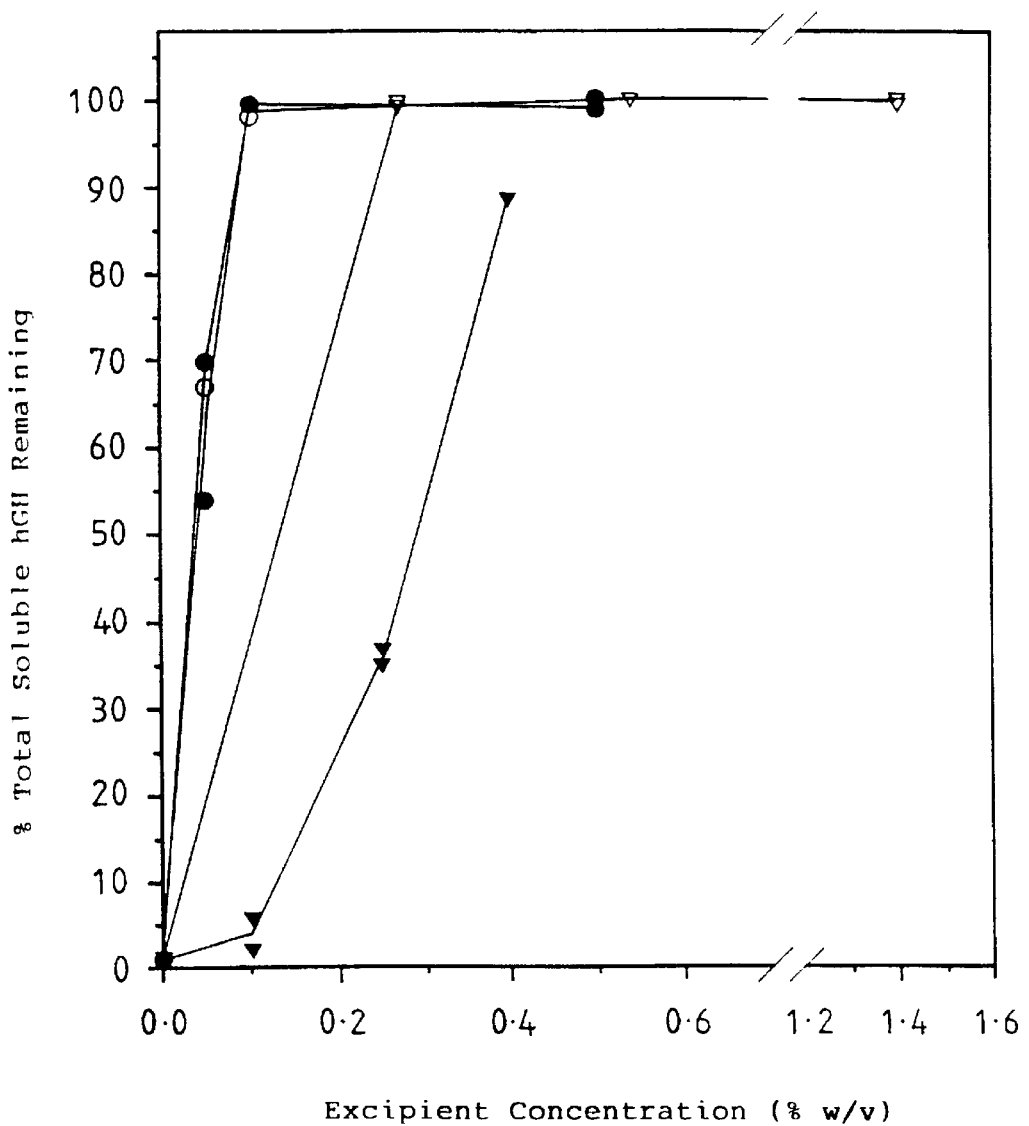
FIG. 3 summarizes graphically the ability of various stabilizing agents to reduce the precipitation of aggregated hGH induced through interfacial stress (vortex agitation).

FIG. 3 shows the effect of excipients (% w/v) on aggregation of hGH (1.5 mg/ml in 5 mM phosphate buffer, pH 5.6) induced through interfacial stress by vortexing at constant speed for 60 s as described in FIG. 2. The data represent the percentage of total soluble hGH (monomer plus higher order aggregated species) remaining after treatment expressed as a percentage relative to the peak area due to hGH from SEC analysis in the appropriate control solution in the presence of Pluronic F-68 (○), Pluronic F-127 (●), sodium taurocholate (▽) or HPMC (▼).

In the absence of excipients, less than 1% hGH remained in solution. Addition of Pluronic polyols, taurocholate or HPMC resulted in a substantial increase in soluble hGH remaining. Pluronics F-68 and F-127 and taurocholate, in particular, provided near quantitative protection of hGH against aggregation.

Example 3

Figure 4:
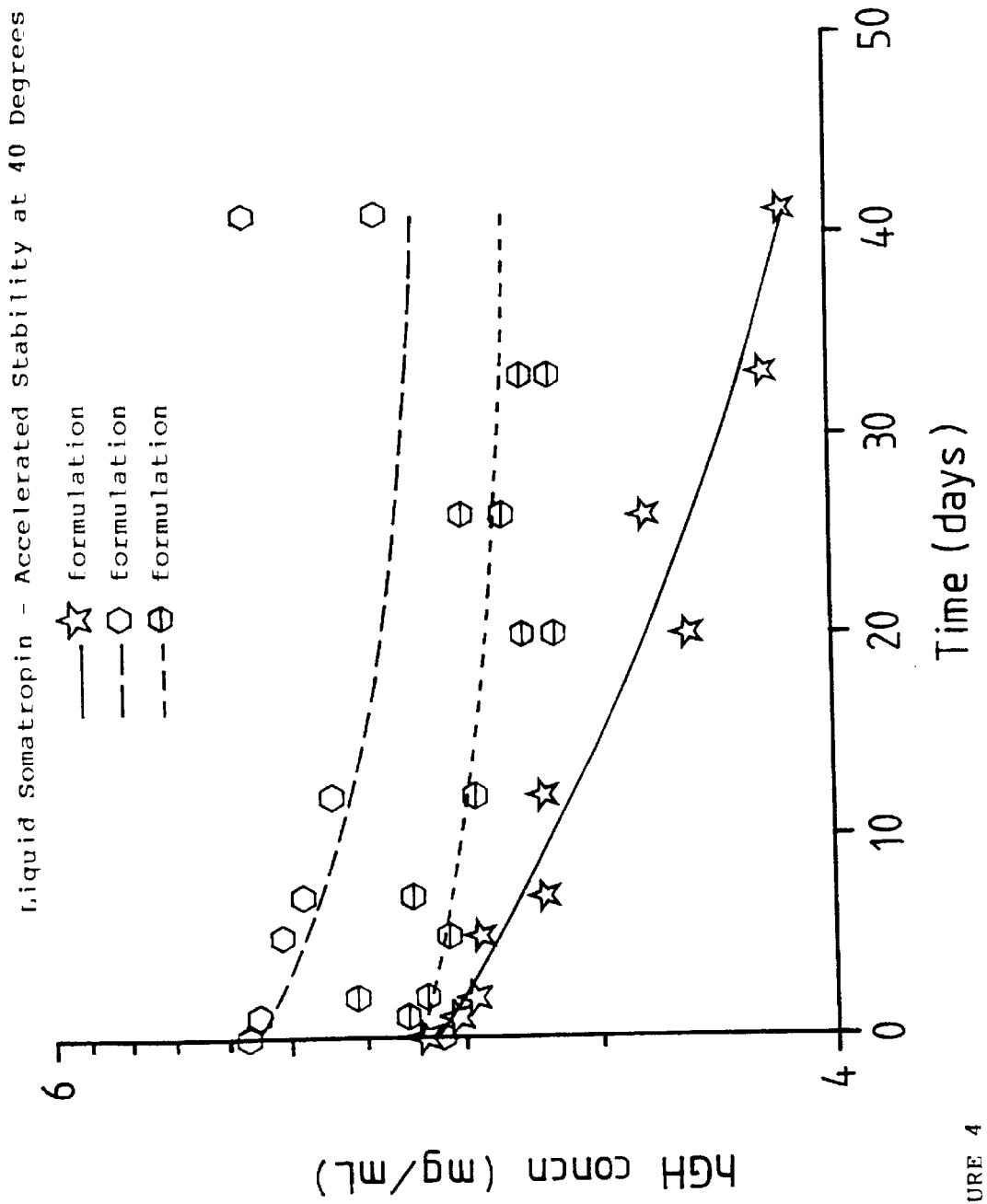
FIG. 4 shows stability of two hGH (5 mg/ml) formulations which differ only in the method of introducing the hGH to the excipients, and a third hGH formulation to which 0.005% w/v EDTA has been added.

FIG. 4 shows effect of method of formulation on stability of hGH formulations. Formulation 1 was prepared by concentrating purified hGH solution to 7–7.5 mg/mL and adding a two-fold concentrate of a solution containing all the excipients adjusted to a pH which produces a liquid formulation of pH 5.6 without further adjustment, and a final adjustment with water to achieve a final hGH concentration of 5 mg/ml.

Formulation 2 was prepared by buffer exchange, and purified hGH solution was concentrated to the desired concentration by exchange into a buffer which contained all the excipients (except Pluronic F-68) at the required concentration. Sufficient solid Pluronic F-68 was then added to give the required concentration. The pH was then checked and adjusted if necessary.

Formulations 1 and 2 have the same specifications:

| | |
|---|---|
| hGH (Somatropin) | 5 mg |
| citric acid monohydrate | 2.04 mg/mL |
| trisodium citrate dihydrate | 2.85 mg/mL |

-continued

| | |
|---|---|
| sodium chloride | 6.23 mg/mL |
| sodium hydroxide | 0.388 mg/mL |
| benzyl alcohol | 0.9% |
| Pluronic F-68 | 0.08% |
| pH | 5.6 |

Formulation 3 was prepared as for formulation 2 to the same specifications as formulations 1 and 2, with the addition of 0.005% w/v EDTA.

Formulations 1 to 3 were stored at 40° C. and tested for hGH content by size exclusion HPLC at intervals over 40 days. As shown in FIG. 4, formulation 2 and 3 showed superior stability, particularly in comparison with formulation 1, in this accelerated stability test at 40° C.

What is claimed is:

1. A method for the preparation of a stable, liquid formulation of growth hormone, comprising growth hormone, a buffer and at least one stabilizer selected from the group consisting of:

(i) polyoxyethylene-polyoxypropylene block copolymer non-ionic surfactants, (ii) taurocholic acid or salts or derivatives thereof, and (iii) methyl cellulose derivatives, wherein the method comprises the step of adding said buffer and stabilizer(s) to a solution of growth hormone such that the growth hormone is not exposed to concentrations of said buffer or stabilizer(s) that are greater than two times the final concentrations of said buffer or stabilizer(s) in the formulation, such that the formulation is suitable for prolonged storage at temperatures below and above freezing.

2. A method according to claim 1, wherein the growth hormone is human growth hormone.

3. A method according to claim 1, wherein the stabilizer(s) are selected from the group consisting of Pluronic polyols, taurocholic acid and its salts, and hydroxypropylmethyl cellulose.

4. A method according to claim 1, wherein the formulation comprises 0.08% w/v of a Pluronic polyol as the stabilizer(s).

5. A method according to claim 1, wherein the stabilizer(s) is added to the formulation immediately prior to final volume adjustment.

6. A method according to claim 1, wherein the formulation comprises 0.01–5.0% w/v of the stabilizer(s).

7. A method according to claim 6, wherein the formulation comprises 0.05%–2.0% w/v of the stabilizer(s).

8. A method according to claim 7, wherein the formulation comprises 0.08%–1.0% w/v of the stabilizer(s).

9. A method according to claim 1, wherein the pH of the formulation is from 5.0 to 7.5.

10. A method according to claim 9, wherein the pH of the formulation is from 5.0to 6.8.

11. A method according to claim 10, wherein the pH of the formulation is from 5.2–6.5.

12. A method according to claim 11, wherein the pH of the formulation is from 5.4–5.8.

13. A method according to claim 1, wherein the formulation comprises a pharmacologically acceptable buffer at a concentration of 2.5 to 50 mM.

14. A method according to claim 13, wherein said buffer is a phosphate buffer.

15. A method according to claim 13, wherein said buffer is a citrate buffer.

16. A method according to claim 13, wherein the formulation comprises a pharmacologically acceptable buffer at a concentration of 10–20 mM.

17. A method according to claim 16, wherein said buffer is a phosphate buffer.

18. A method according to claim 16, wherein said buffer is a citrate buffer.

* * * * *